(12) United States Patent  (10) Patent No.: US 7,917,311 B2
Finkel et al.  (45) Date of Patent: Mar. 29, 2011

(54) METHOD FOR STRUCTURAL HEALTH MONITORING USING A SMART SENSOR SYSTEM

(75) Inventors: Peter Finkel, Downingtown, PA (US); Michael W. Barsoum, Moorestown, NJ (US); Sandip Basu, Secane, PA (US); Aiguo Zhou, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 314 days.

(21) Appl. No.: 12/130,234

(22) Filed: May 30, 2008

(65) Prior Publication Data
US 2009/0055106 A1    Feb. 26, 2009

Related U.S. Application Data

(60) Provisional application No. 60/941,865, filed on Jun. 4, 2007.

(51) Int. Cl.
*G01B 5/28*    (2006.01)
(52) U.S. Cl. .......................................................... 702/39
(58) Field of Classification Search .................... 702/35, 702/36, 39, 159
See application file for complete search history.

(56) References Cited

U.S. PATENT DOCUMENTS

| 3,577,774 | A | * | 5/1971 | Steffens et al. ................. 73/597 |
| 3,585,865 | A | * | 6/1971 | Bungart et al. ................. 73/632 |
| 4,694,698 | A | | 9/1987 | Miyajima |
| 6,996,480 | B2 | | 2/2006 | Giurgiutiu et al. |
| 7,075,424 | B1 | | 7/2006 | Sundaresan et al. |
| 2005/0068041 | A1 | | 3/2005 | Kress et al. |

FOREIGN PATENT DOCUMENTS

WO    WO 02/062206 A2    8/2002

OTHER PUBLICATIONS

Lading, Lars, et al., "Fundamentals for Remote Structural Health Monitoring of Wind Turbine Blades—A Preproject", "Annex B-Sensors and Non-Destructive Testing Methods for Damage Detection in Wind Turbine Blades", Riso-R-1341 (EN), Riso National Laboratory, Roskilde, Denmark, May 2002, pp. 36-37.
Giurgiutiu, Victor, et al., "Recent Advancements in the Electro-Mechanical (E/M) Impedance Method for Structural Health Monitoring and NDE", Paper # 3329-53 at the SPIE's 5th Annual International Symposium on Smart Structures and Materials, Mar. 1998, pp. 1-12.
Barsoum, M.W., Shen, T., Kalidindi, S.R., et al.,"Fully Reversible, Dislocation-Based Compressive Deformation of Ti3SiC2 to 1 GPa", Nature Materials, 2, 2003, 107-111.

(Continued)

*Primary Examiner* — Drew A Dunn
*Assistant Examiner* — Stephen J Cherry
(74) *Attorney, Agent, or Firm* — Knoble, Yoshida & Dunleavy, LLC

(57) ABSTRACT

The structural health monitoring method of the present invention utilizes a sensor system to determine information about deformation, stress and/or damage in structural elements. The sensor system and the method employ at least one sensor which comprises a material having fully-reversible nonlinear elasticity. The method comprises associating at least one sensor including a material having fully-reversible nonlinear elasticity with a structural element in a manner whereby stress is transferred from said structural element to said sensor, propagating ultrasound through a portion of the sensor, receiving the ultrasound which has been propagated through at least a portion of the sensor and determining information about the structural element from attenuation and/or time of flight of said received ultrasound.

24 Claims, 6 Drawing Sheets

OTHER PUBLICATIONS

Barsoum, M.W., Murugaiah, A., Kalidindi, S.R., et al., "Kink Bands, Nonlinear Elasticity and Nanoindentations in Graphite", Carbon, 42, 2004, 1435-1445.

Barsoum, M.W., Murugaiah, A., Kalidindi, S.R., et al., "Kinking Nonlinear Elastic Solids, Nanoindentations, and Geology", Phys. Rev. Lett., 92, 2004, 255508-1-255508-4.

Barsoum, M.W., Shen, T., Zhou, A., et al., "Microscale Modeling of Kinking Nonlinear Elastic Solids", Phys. Rev. B., 71, 2005, 134101-1-134101-8.

Murugaiah, A., Barsoum, M.W., Kalidindi, S.R., et al., "Spherical Nanoindentations and Kink bands in Ti3SiC2", J. Mater. Res., 19, 2004, 1139-1148.

Zhen, T., in Department of Materials Science and Engineering. (Drexel University, Philadelphia, 2004).

Radovic, M., Barsoum, M.W., El-Raghy, T., et al., "Effect of Temerature, Strain Rate and Grain Size on the Mechanical Response of Ti3SiC2 in Tension", Acts Materialia, 50, 2002, 1297-1306.

Jovic, V.D., and Barsoum, M.W., "Corrosion Behavior and Passive Film Characteristics Formed on Ti, Ti3SiC2, and Ti4AlN3 in H2SO4 and HCl", J. Electrochem. Soc., 151, 2004, B71-B76.

Bhalla, S., and Soh, C.K., "High Frequency Piezoelectric Signatures for Diagnosis of Seismic/Blast Induced Structural Damages", NDT&E International, 37, 2004, 23-33.

Zhou, A.G., Basu, S., Barsoum, M.W., "Kinking Nonlinear Elasticity, Damping and Microyielding of Hexagonal Close-Packed Metals", Acta Materialia, 56, Nov. 5, 2007, 60-67.

\* cited by examiner

METHOD FOR STRUCTURAL HEALTH MONITORING USING A SMART SENSOR SYSTEM

STATEMENT OF GOVERNMENT INTEREST

This invention was reduced to practice with Government support under Grant No. DAAD19-03-1-0213 awarded by Army Research Office; the Government is therefore entitled to certain rights to this invention.

BACKGROUND OF THE INVENTION

1. Field of the Invention

The present invention relates to a method for structural health monitoring (SHM) using a sensor system and ultrasound. The sensor system may be used to monitor the structural health of structures including civil engineering structures, such as bridges, buildings and underwater structures, critical structural elements in the automobile, aerospace and petrochemical industry as well as storage structures and reactors.

2. Description of the Related Technology

SHM is used to maintain and preserve the structural integrity of structures, which degrade over time from exposure to excipient factors, such as earthquakes, storms, pollution, vibration, traffic, and other environmental factors. In the last few decades there has been tremendous interest in developing methods and sensors, such as strain gages, displacement sensors, accelerometers, magneto-strictive sensors, fiber optic sensors and piezoelectric sensors, for detecting structural degradation or damage.

Current SHM techniques utilize either global sensing methods or local sensing methods. Global dynamic methods excite a structure using low frequency acoustic waves and detect the resulting corresponding natural frequencies of the structure. The natural frequency data may then be manipulated with various algorithms to locate and quantify damage in simple structures. Global dynamic methods, however, rely on a relatively small number of low order modes that are insufficiently sensitive to detect localized incipient damage, which may be critical to structural integrity. Additionally, the application and detection of low frequency excitation, typically below 100 Hz, is easily contaminated by surrounding vibrations and noise. Global static methods, such as static displacement response and static strain measurement, are also impractical since they are too expensive to enable a cost and time efficient structural evaluation.

Local sensing methods, such as ultrasonic wave propagation techniques, acoustic emissions, magnetic field analysis, electrical methods, dye penetrant testing, impact echo testing and X-ray radiography, are also problematic. A common limitation of local sensing methods is that a probe needs to be moved around the structure to first identify a potential site of structural damage if the location of structural weakness is not already known. Attempts to overcome this difficulty, with varying success, included measuring the response from an array of piezoelectric patches on the surface, magneto-elastic sensors and fiber Bragg grating methods.

Of the various local sensing methods, ultrasonic wave propagation is one of the most promising, enabling detection of damage and structural flaws with a high degree of sensitivity. Examples of ultrasonic wave propagation are disclosed in U.S. Pat. No. 6,996,480 and Lars Lading, et al., "Fundamentals for Remote Structural Health Monitoring of Wind Turbine Blades", Riso National Laboratory, 2002. The main drawback of the ultrasonic method is that it requires several transducers to be installed at various locations to monitor a particular structure due to the attenuation and absorption of sound waves in these structures. Often, ultrasonic transducer installation is time-consuming and expensive making such methods impractical.

Ultrasonic methods also typically require complex data processing. In addition to being expensive, ultrasonic methods also render the structure unavailable for use throughout the duration of the test. Due to the nature of sound waves, excitation means for the ultrasonic transducers has to be coupled directly onto the structure being monitored. In addition, such systems typically only work over relatively narrow temperature ranges and under limited environmental conditions.

In spite of recent innovations, as far as the inventors are aware, no sensor, to date, enables highly sensitive detection of various types of deformation under a wide range of variable atmospheric, corrosive and temperature conditions. Current sensors additionally require complex data processing and large amounts of information to analyze structural deformation. Therefore, there is a need to develop a sensor system capable of extracting important parameters from minimal amounts of data using simple data processing techniques and which is further capable of highly sensitive detection irrespective of environmental conditions.

SUMMARY OF THE INVENTION

In one aspect, the present invention relates to a method for structural health monitoring using ultrasonic wave propagation through a system including one or more smart sensor elements comprising at least one material which exhibits fully-reversible nonlinear elasticity (FRNE).

Another aspect of the invention is directed to a method comprising operatively associating at least one smart sensor element with a structure, propagating ultrasound through the smart sensor element, receiving the ultrasound propagated through the smart sensor element, and determining information relating to the structure from the attenuation and/or the speed of the received ultrasound. The smart sensor element comprises at least one material which exhibits fully-reversible nonlinear elasticity (FRNE).

Another aspect of the invention is directed to a sensor system comprising at least one smart sensor, an ultrasound emitter and a receiver for receiving ultrasound propagated through the sensor.

Another aspect of the invention is applicable if the structural component itself, is made of a material that exhibits fully-reversible nonlinear elasticity (FRNE), in which case it can be monitored directly using ultrasound.

vs. c/a.

Figure 4:
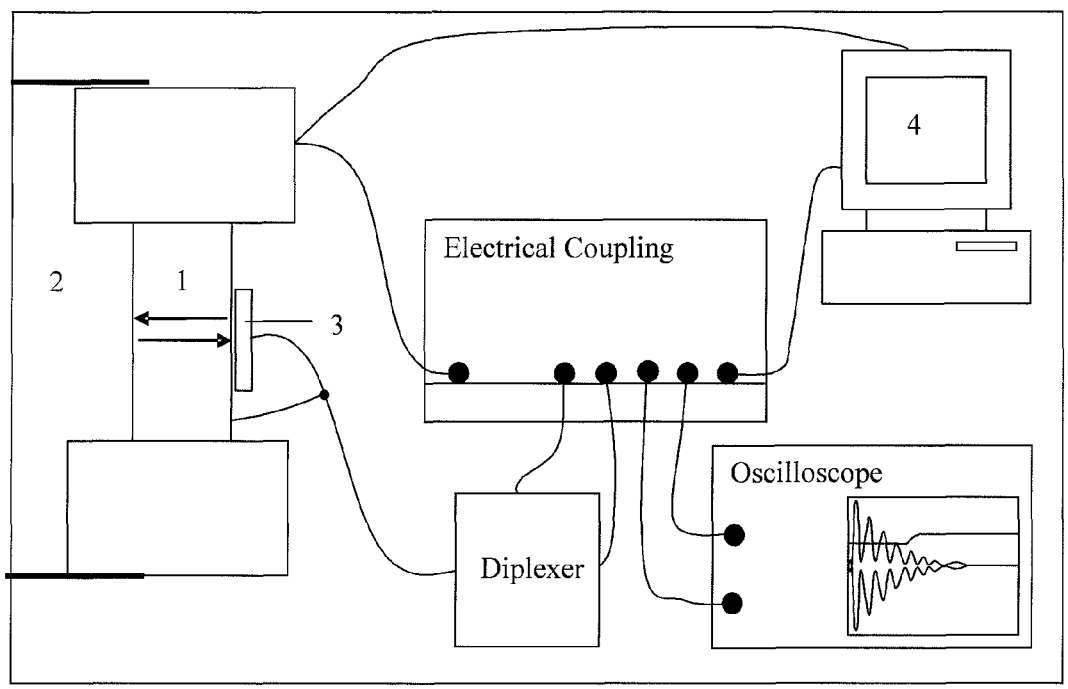

FIG. 4 is a schematic of an ultrasonic sensor system in accordance with the present invention.

Figure 5:
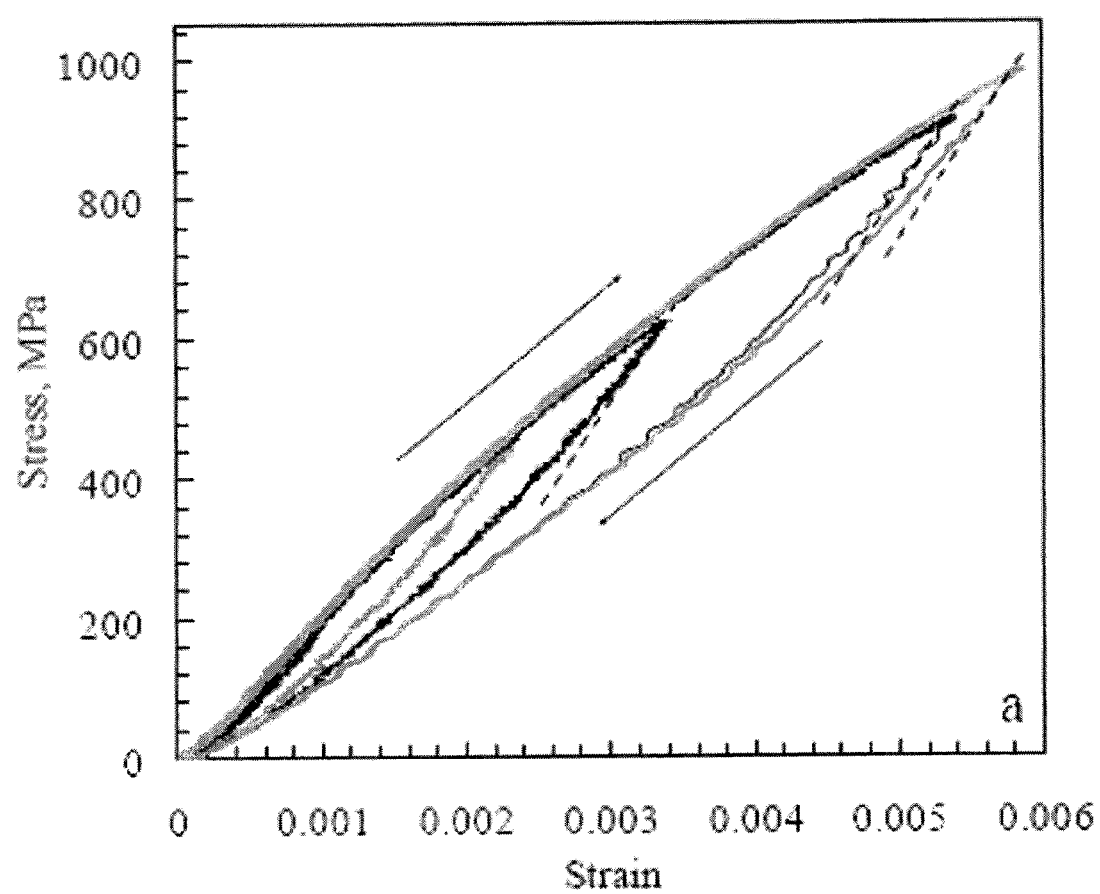

FIG. 5 is a graph of fully reversible hysteretic stress-strain behavior of $Ti_3SiC_2$.

Figure 6:
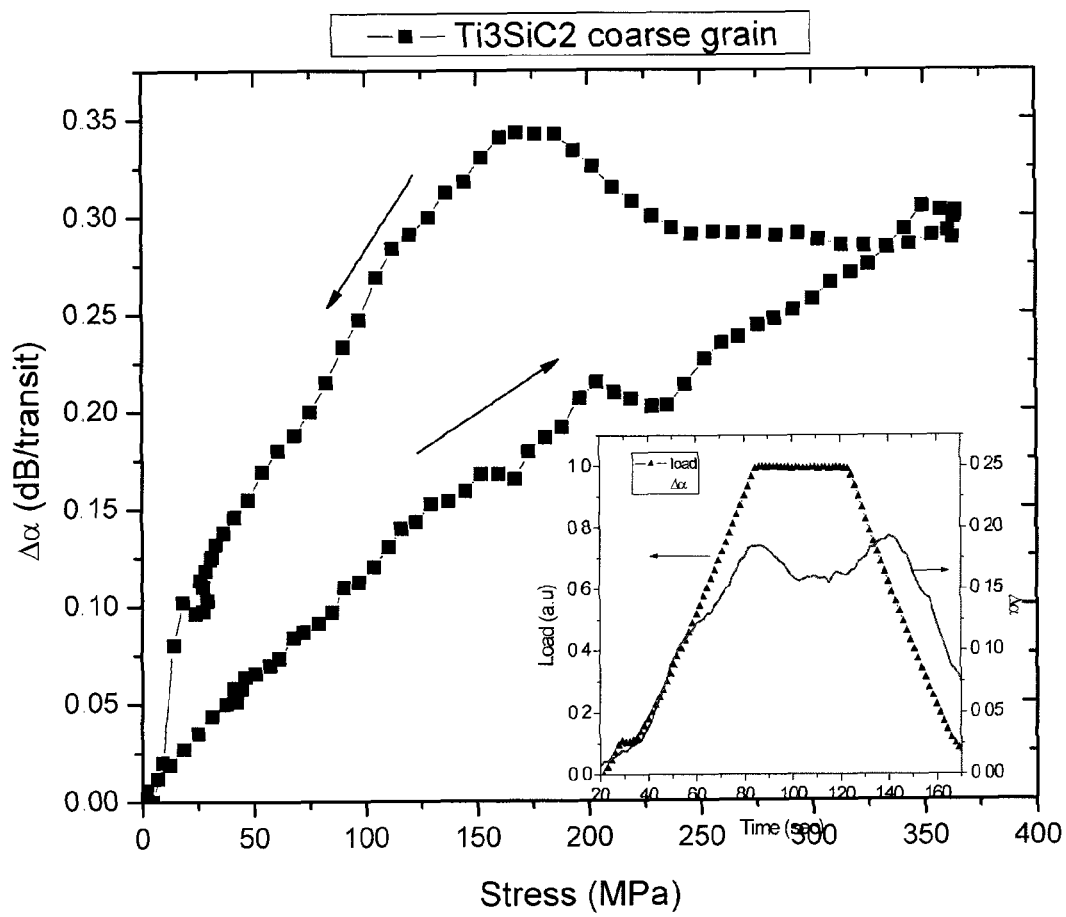

FIG. 6 is a graph of ultrasound attenuation versus stress for coarse-grain $Ti_3SiC_2$ under load.

DETAILED DESCRIPTION OF THE PREFERRED EMBODIMENTS

In one aspect, the invention is directed to a method for structural health monitoring (SHM) of materials using ultrasound and a smart sensor system. The method involves operatively associating at least one smart sensor element 1 including at least one material which has a fully-reversible nonlinear elasticity (FRNE)[3], with a surface of a structure or structural element 2 and using an ultrasonic transducer to propagate ultrasound through the smart sensor element 1. As the structure 2 degrades over time, structural stresses will be physically transferred to the sensor 1. By monitoring and recording changes in the ultrasound attenuation and/or time of flight of ultrasound propagated through sensor 1 by means of ultrasonic transducer 3, it is possible to determine one or more of the presence of, location of and severity of damage to the structure, as well as generate an image of the structural damage by using a properly spaced array of sensors 1.

Sensor 1 should be associated with the structural element 2 in a manner whereby deformation of structural element 2 causes a corresponding deformation of sensor 1. Thus, it is often desirable to have a surface of sensor 1 maintained in direct contact with a surface of structural element 2 for this purpose. Any suitable means for maintaining sensor 1 in association with structural element 2 may be employed. In one embodiment, sensor 1 may be bonded to structural element 2. This bond is sufficiently secure so as to essentially prevent relative movement between a sensor 1 and structural element 2 to thereby provide excellent transmission of stress from structural element 2 to sensor 1. In another embodiment, sensor 1 may be clamped to structural element 2.

One aspect of the SHM method and the sensor system of the present invention involves selecting an appropriate material for use in sensor 1. The material should have FRNE characteristics to enable sensor 1 to record and reconstruct the applied stress and deformation of a structure over time. This deformation phenomenon may be partially attributed to the reversible formation and the disassociation of incipient kink bands (IKB). Such materials are sometimes referred to as kinking nonlinear-elastic materials or KNE materials.

Figure 1A:
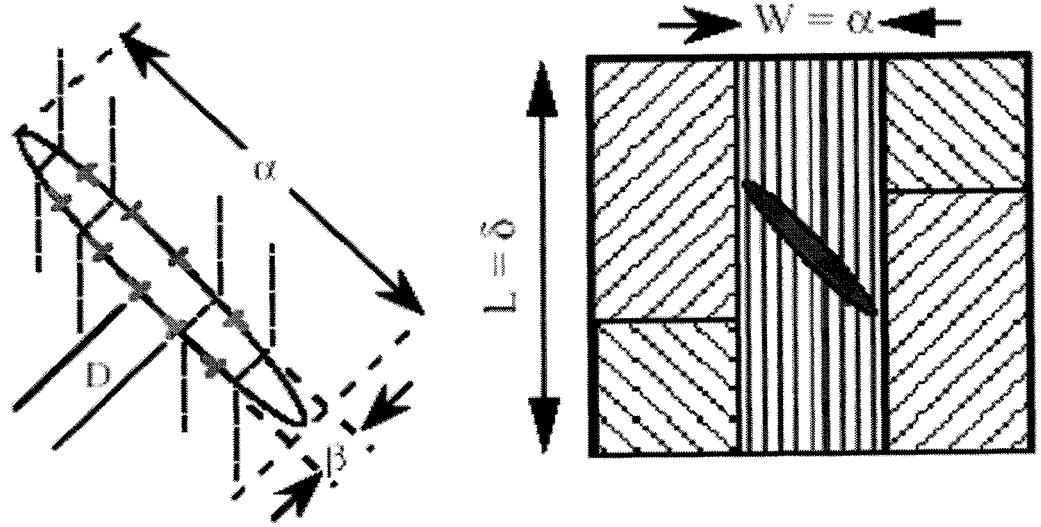
FIG. 1(a) is a schematic showing the formation of incipient kink bands.

FIG. 1(a) shows that as a KNE material is stressed, IKBs having approximately parallel walls of opposite sign dislocations that are not dissociated, i.e. still attracted to each other at their ends, are formed prior to the generation of regular kink bands (KB). The IKBs dissociate when the load is very high and produce mobile dislocation walls (MDW), shown in FIG. 1(b), which lead to permanent deformation. Once the MDW coalesce, kink boundaries are formed and subsequently produce the kind band structure depicted in FIG. 1(c).- It is important to note that this invention is not restricted to the micromechanisms shown in FIG. 1. Any solid in which fully reversible dislocation motion occurs—such as dislocation pileups in plastically anisotropic solids—can be used for this invention. The key aspect is fully reversible dislocation motion.

Figure 1B:
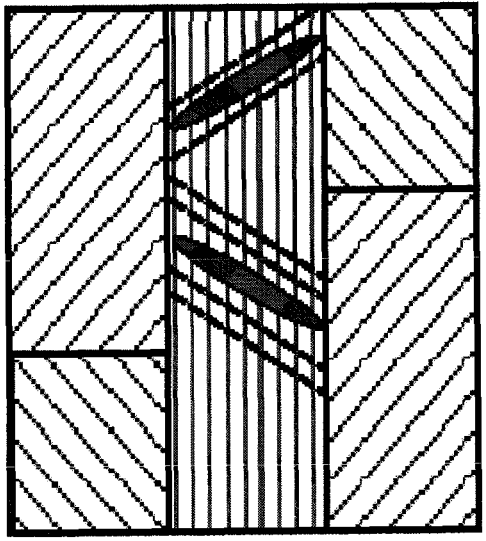
FIG. 1(b) is a schematic showing mobile dislocation walls.
Figure 1C:
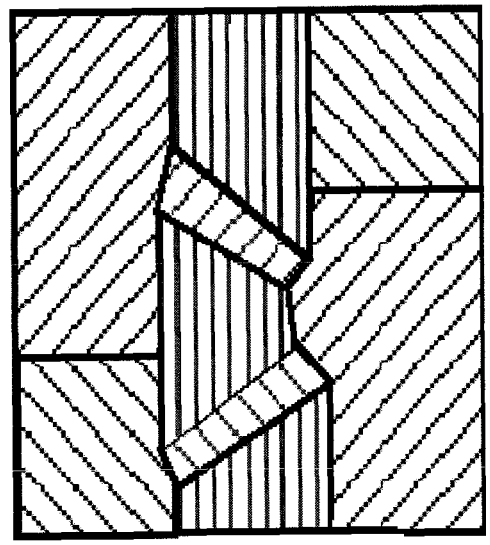
FIG. 1(c) is a schematic showing permanent kink bands.
Figure 2:
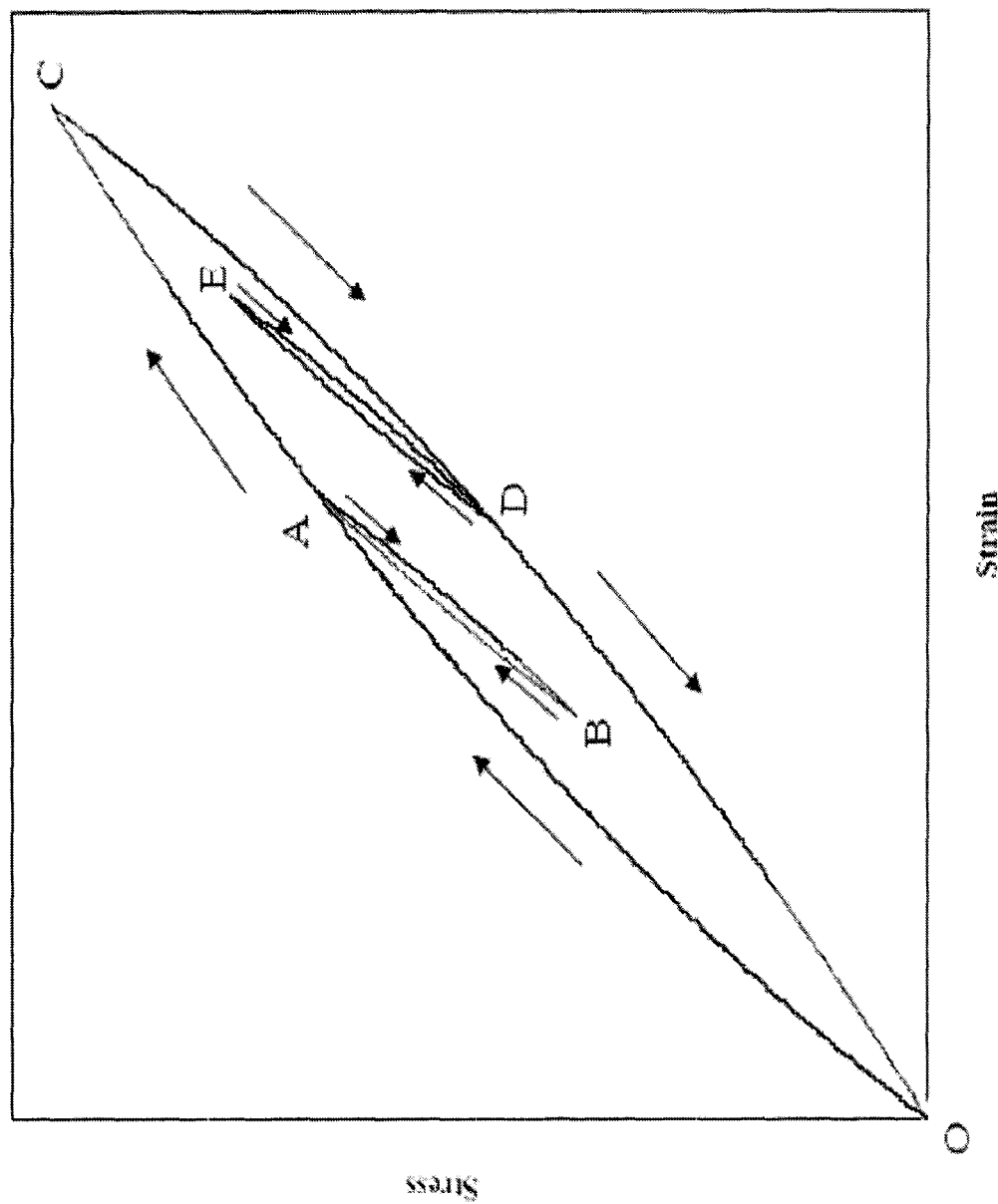
FIG. 2 is a schematic diagram of a complex loading unloading stress-strain response of a kinking nonlinear elastic solid. The arrows in the figure represent the loading direction.

The characterizing feature of KNE material deformation suitable for the sensor elements of the present invention is the formation of fully reversible, rate-independent, closed hysteresis loops in stress-strain curves, delineates deformation process described in FIG. 1(a)-1(c). These loops are strongly influenced by grain size, with the energy dissipated per unit volume per cycle, $W_d$, being significantly larger in the coarse-grained material. As the stresses become larger, the hysteresis loops become larger until the structure fails. FIG. 2 demonstrates a complex loading and unloading stress-strain response of KNE solids, which are stress memory materials capable of remembering the highest and/or lowest points of these hysteresis loops or cycles.

KNE solids are further characterized by plastic anisotropy, which typically occurs in materials having high c/a ratio, and/or a complicated multi-atom unit cells. Plastic anisotropy only allows for deformation by slip on one easy slip system, which for hexagonal solids is basal slip. Dislocation motion on other slip systems is very difficult. The plastic anisotropy due to high c/a ratio only allows for dislocations on one easy slip system. Any other kinds of dislocations are of extremely low probability and thus are insignificant.

Figure 3:
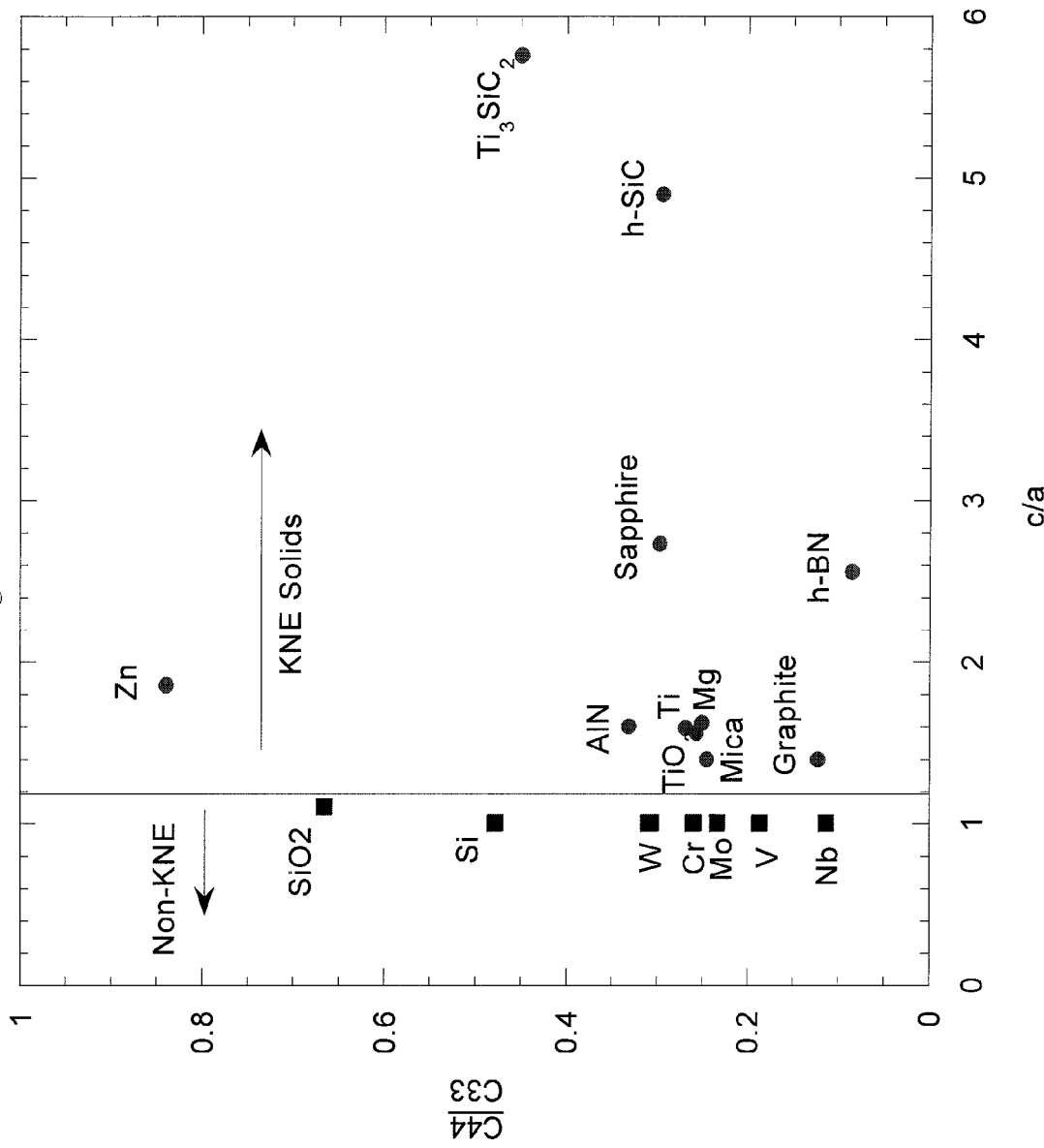
FIG. 3 is a graph of $$\frac{c_{44}}{c_{33}}$$

FIG. 3 identifies materials capable of kinking non-linear deformation by graphing $C_{44}/C_{33}$ versus c/a. KNE solids having a large c/a ratio lie to the right of the vertical line. Materials having a c/a ratio of above about 1.2 may be suitable for use in the present invention if they exhibit fully-reversible nonlinear elasticity. More preferably, materials having a c/a ratio above about 1.5 are employed. Solids that allow for more than one slip system are typically unsuitable for fabricating the sensor 1 of the present invention. KNE solids that exhibit FRNE should thus have a c/a ratio of at least 1.2, more preferably, the c/a ratio should be at least 1.5. There is no upper limit on the c/a ratio since the higher the c/a ratio, the better the material will perform as a sensing element.

In one embodiment, sensor 1 is constructed from at least one KNE solid that is stable over a temperature range of about 4 K to about 1000 K, more preferably over a temperature range of about 77 K to about 1000 K and most preferably over a temperature range of about 123.15 K to about 973.15 K. In another embodiment, the KNE solid is chemically stable, inert and resistant to aggressive environmental and atmospheric conditions. More preferably, the KNE solid is generally corrosion resistant, and most preferably, the KNE solid is specifically resistant to acidic, basic, salt containing and other corrosive atmospheres such as S-containing ones.

Any material exhibiting FRNE behavior and have a c/a ratio above about 1.2, preferably, above about 1.5 can be used as a sensor material depending on the maximum possible stress, temperature and ambient conditions that the material can withstand without undergoing significant alterations. Sensor 1 may be configured in various shapes to increase the working range of stress and/or strain according to the requirements of the structural element 2.

In an exemplary SHM method of the present invention, at least one sensor 1 containing a material exhibiting FRNE behavior is clamped to a portion of a structural element 2. Optionally, the method includes a preliminary step of identifying a defect, damage or stress within structural element 2 or identifying a particular portion of structural element 2 for which monitoring is desirable, using any standard technique. Sensor 1 can be employed in conjunction with a suitable system, to detect and image stress and damage within structural element 2. Alternatively, sensor 1 may be used in a sensor system to detect inherent defects in structural element 2.

In one embodiment, a conventional ultrasound sensor can be used to measure the inherent/existing defects in structural element 2 prior to installation of the sensing system of the present invention. After installation of the sensing system of the present invention, the sensing system will measure how the existing inherent defects grow or change by detecting the changing stress-state in the structural element 2.

As shown in FIG. 4, sensor 1 may be associated with a structural element 2 by bonding or using a clamp or other suitable means such that structural deformation and stress can be effectively transmitted from structural element 2 to sensor 1. The securing means should also enable secure long-term retention of sensor 1 on structural element 2. In a preferred embodiment, hardened steel clamps can be employed for associating sensor 1 with structural element 2 for application in bridges or civil structures; and the clamp can be a hard ceramic if the application temperature is high and/or the atmosphere is corrosive.

Sensor 1 may be calibrated by propagating an ultrasonic pulse through sensor 1 to obtain an initial calibration of the state of sensor 1 for use as a baseline to monitor the state of structural element 2. As structural element 2 deforms, is stressed or degrades over time, the deformation and/or stress will be physically transferred from structural element 2 to sensor 1. Ultrasonic pulses may be periodically propagated through sensor 1 to obtain measurements and monitor the condition of structural element 2 relative to the baseline condition measured during calibration of sensor 1.

It is the intention that the ultrasonic pulses should pass solely through sensor 1 and not penetrate structural element 2 so as to obtain measurements of the attenuation and time of flight of the ultrasonic pulses, as influenced by sensor 1 only. A transducer 3 optically coupled to sensor 1 emits ultrasonic pulses and may be used to receive the ultrasonic pulses after they have passed through at least a portion of sensor 1. The collected data may be recorded by a data storage unit associated with a data processing unit 4. Data processing unit 4 can generate an accurate image of deformation, stress and/or damage to structural element 2 in real time. Data processing unit 4 may also determine the location of deformation, stress or damage based on time of flight data as well as determine the severity of structural damage using ultrasonic attenuation by sensor 1. In a preferred embodiment, data may be transmitted wirelessly to data processing unit 4. Over time it is possible to generate a history of the changes in structural element 2.

The SHM method and sensor system of the present application are capable of providing significant information regarding structural damage, stress and deformation to structural elements using a minimal amount of data by interpolating the deformation history between two consequent measurements. Furthermore, the sensor system is capable of measuring a wide range of stresses and/or deformation while requiring a relatively minor amount of data processing.

The SHM method and sensor system of the present invention function by capturing ultrasound attenuation, which is used to determine the nonlinear elasticity or reversible dislocation motion within sensor 1. When sensor 1 experiences stress or deformation transferred from structural element 2, IKBs and/or reversible dislocations are nucleated and interact with the ultrasound pulses, causing attenuation and influencing time of flight of the pulses. Upon unloading, the reversible dislocations or IKBs annihilate and the attenuation and time of flight influence is no longer observed. This reversible behavior of stress, ultrasound attenuation and influence on time of flight may be used to determine the induced stress for every point of the hysteretic loop, shown in FIG. 2. Furthermore, the ultrasound attenuation may also be used to determine the maximum stress structural element 2 experienced before failure and to deduce the stress/strain deformation history of structural element 2.

The sensor system of one embodiment of the present invention may be useful for structural health monitoring of numerous structures, particularly civil engineering structures such as bridges, buildings and underwater structures; structural elements of automobiles, trains, aircraft, aerospace devices, watercraft, submersibles and other man made devices and machines; and reactors, storage structures, etc., that degrade with time due to exposure to excipient factors, such as earthquakes, storms, pollution, vibration, traffic, and other environmental factors. The SHM methods and sensor systems of the present invention enable an accurate determination of the integrity of these structures, relative to baseline integrity, at any point in time, and may enable engineers to determine when and where structural repair is necessary. The method of the present invention is equally applicable to historical as well as modem structures and may be used to maintain and preserve structural elements, monitor structural damage over time and warn of impending structural failure. It is envisioned that the SHM method of the present invention may be particularly beneficial to the aerospace, automobile and petrochemical industries.

An example of KNE solids are materials having $M_{n+1}AX_n$- or MAX—phases, where M is an early transition metal, A is an A-group element, X is carbon and/or nitrogen, and n=1–3. The MAX phases, numbering over 50, are ternary carbides and nitrides. The crystal structure of MAX phases comprise hexagonal nets of "A" atoms separated by three nearly close-packed "M" layers that accommodate "X" atoms in the octahedral sites between them. Typically, suitable materials are solid, crystalline materials with a crystal lattice structure. Materials having high temperature capabilities such $Ti_2AlC$, are particularly useful since such materials will be better able to withstand significant atmospheric temperature variations in use.

In another embodiment, the actual structural component is fabricated with a material exhibiting fully-reversible nonlinear elasticity. In which case, the entire part can be used to monitor its health and all that required is to propagate ultrasound through the entire or parts of the structure and measuring its attenuation.

Of the MAX phase compounds, $Ti_3SiC_2$ and $Ti_2AlC$ are some of the most promising, lightweight candidate materials for use in sensing elements suitable for high temperature structural monitoring and other applications. Despite having a density of about 4.5 gm/cm$^3$, $Ti_3SiC_2$ and $Ti_2AlC$ have a stiffness about three times as high as titanium, but are as readily machinable as titanium. With a Vickers hardness of approximately 3 GPa, they are relatively soft, unusually resistant to thermal shock and highly damage tolerant. Unlike most brittle solids, edge cracks do not emanate from the corners of hardness indentations. Rather, intensive kinking, buckling and bending of individual grains take place in the vicinity of the indentations, resulting in pseudo-plastic behavior over a wide range of temperature.

Polycrystalline $Ti_3SiC_2$ are further capable of being cyclically loaded in compression at room temperature to stresses up to 1 GPa, and fully recover on the removal of the load, while dissipating about 25% (0.7 MJm$^{-3}$) of the mechanical energy, as shown in FIG. 5. These loss factors are higher than most woods, and comparable to polypropylene and nylon. FIG. 5 depicts the typical behavioral plot of a structure composed of coarse-grained $Ti_3SiC_2$. The stress-strain curve delineates a fully reversible, rate-independent, closed hysteresis loop characteristic of KNE solids. Furthermore, $Ti_2AlC$, graphite, hexagonal-boron nitride, most of the hexagonal metals and mica have similar deformation behavior, which can be attributed to the reversible formation of dislocations and can be used to fabricate sensing elements in accordance with the present invention if the particular material is suitable for the stress, temperature and atmospheric conditions to which it will be subjected in use.

The behavior of the KNE materials allows use of a calibration curve similar to that shown in FIG. 6, to correlate ultrasound attenuation by the KNE materials with the stress exerted on sensor 1. In addition, since KNE materials exhibit reversible deformation but provide a different response as a result of such reversible deformation, additional information such as the prior maximum deformation and deformation history can be obtained from the ultrasound attenuation data obtained from the KNE materials. This can be seen in, for example, FIG. 6, where, upon reduction of the applied stress on the KNE material, the attenuation followed a different curve (downward arrow) than was followed during application of the applied stress (upward arrow) to the KNE material.

This behavior of the KNE material also permits imaging of the deformation, stress or damage to a structural element since the information required for such imaging can be obtained by comparison to a calibration curve and/or via application of simple algorithms to correlate ultrasound attenuation and/or time of flight with specific structural stress and/or damage in the structural element.

References cited herein are listed below and the disclosures of the listed references are hereby incorporated by reference in their entirety:

1 C. Hison, G. Ausanio, A. C. Barone, et al., Sensors and Actuators A 125, 10 (2005).
2 T. J. Johnson, R. L. Brown, D. E. Adams, et al, Mechanical Systems and Signal Processing 18, 555 (2004).
3 M. W. Barsoum, T. Zhen, S. R. Kalidindi, et al., Nature Materials 2, 107 (2003).
4 M. W. Barsoum, Prog. Solid State Chem 28, 201 (2000).
5 M. W. Barsoum and T. El-Raghy, J. Amer. Cer. Soc. 79, 1953 (1996).
6 M. W. Barsoum and T. El-Raghy, American Scientist 89, 336 (2000).
7 M. W. Barsoum and M. Radovic, in *Encyclopedia of Materials Science and Technology*, edited by R. W. C. K. H. J. Buschow, M. C. Flemings, E. J. Kramer, S. Mahajan and P. Veyssiere (Elsevier, Amsterdam, 2004).
8 W Jeitschko and H. Nowotny, Monatsh. fur Chem., 98 329 (1967).
9 P. Pampuch, J. Lis, L. Stobierski, et al., J. Eur. Ceram. Soc. 5, 283 (1989).
10 T. El-Raghy, M. W. Barsoum, a. Zavaliangos, et al., J. Amer. Cer. Soc. 82 2855 (1999).
11 T. El-Raghy, A. Zavaliangos, M. W. Barsoum, et al., *J. Amer. Cer. Soc.* 80, 513 (1997).
12 A. G. Zhou, M. W. Barsoum, S. Basu, et al., Acta Mater. 54, 1631 (2006).
13 M. W. Barsoum, A. Murugaiah, S. R. Kalidindi, et al., Carbon 42, 1435 (2004).
14 M. W. Barsoum, A. Murugaiah, S. R. Kalidindi, et al., Phys. Rev. Lett. 92, 255508 (2004).
15 M. W. Barsoum, T. Zhen, A. Zhou, et al., Phys. Rev. B. 71, 134101 (2005).
16 A. Murugaiah, M. W. Barsoum, S. R. Kalidindi, et al., J. Mater. Res. 19, 1139 (2004).
17 E. Orowan, Nature 149, 463 (1942).
18 F. C. Frank and A. N. Stroh, Proc. Phys. Soc. 65, 811 (1952).
19 M. W. Barsoum, L. Farber, T. El-Raghy, et al., Met. Mater. Trans. 30A, 1727 (1999).
20 L. Farber, I. Levin, and M. W. Barsoum, Phil. Mag. Letters, 79, 163 (1999).
21 T. Zhen, in *Department of Materials Science and Engineering* (Drexel University, Philadelphia:, 2004).
22 M. Radovic, M. W. Barsoum, T. El-Raghy, et al., Acts Materialia 50, 1297 (2002).
23 M. Radovic, A. Ganguly, M. W. Barsoum, et al., Sub. for pub.
24 V. D. Jovic and M. W. Barsoum, J. Electrochem. Soc. 151, B71 (2004).
25 V. D. Jovic, M. W. Barsoum, B. M. Jovic, et al., Sub. for pub.
26 S. Bhalla and C. K. Soh, NDT&E International 37, 23 (2004).
27 D. M. McCann and M. C. Forde, NDT&E International 34, 71 (2001).
28 H. A. Winston, F. Sun, and B. S. Annigery, J. Engg. for Gas Turbines and Power 123, 353 (2001).
29 J. Leng and A. Asundi, Sensors and Actuators A 103, 330 (2003).
30 A. G. Zhou, S. Basu and M. W. Barsoum, "Kinking Nonlinear Elasticity, Damping and Microyielding of Hexagonal Closed-Packed Metals", *Acta Mater.*, 59, 60-67 (2008).

The invention claimed is:

1. A method for monitoring a structure comprising:
propagating ultrasound through at least a portion of a sensor associated with the structure in a manner whereby stress in the structure is transferred to said sensor;
receiving the ultrasound after it has propagated solely through said portion of the sensor, and
determining information relating to said structure from at least one of attenuation and time of flight of said received ultrasound, wherein said portion of said sensor comprises at least one material having fully-reversible nonlinear elasticity.

2. The method of claim 1, wherein said sensor is capable of operating within a temperature range of about 4 K to about 1000 K.

3. The method of claim 1, wherein said sensor is capable of operating within a temperature range of about 77 K to about 1000 K.

4. The method of claim 1, wherein said sensor is capable of operating within a temperature range of about 123.15 K to about 973.15 K.

5. The method of claim 1, wherein said sensor is corrosion resistant.

6. The method of claim 1, wherein said material having fully-reversible non-linear elasticity is selected from the group consisting of materials having MAX phases.

7. The method of claim 6, wherein the material having fully-reversible non-linear elasticity is selected from the group consisting of $Ti_3SiC_2$, $Ti_2AlC$, graphite, hexagonal-boron nitride, mica, and hexagonal metals.

8. The method of claim 7, wherein the hexagonal metal is selected from the group consisting of Co, Mg, and Ti.

9. The method of claim 1, further comprising a step of identifying a site of deformation, stress or damage in the structure prior to associating the sensor with the structure.

10. The method of claim 1, wherein said method provides a maximum stress said structure experienced before a potential occurrence of structural failure.

11. The method of claim 1 wherein said method provides a deformation history of said structure.

12. The method of claim 1, wherein said method provides an image of deformation, stress or damage to said structure.

13. The method of claim 1, wherein said information about said structure is determined from attenuation of said ultrasound by said sensor.

14. The method of claim 1, wherein said information about said structure is determined from time of flight of said ultrasound through said sensor.

15. The method of claim 1, wherein said sensor is bonded or clamped to said structure.

16. The method of claim 1, wherein said sensor material has a c/a ratio of at least 1.5.

17. A sensor system for monitoring a structure comprising:
at least one sensor, wherein said sensor comprises at least one or more materials having fully-reversible nonlinear elasticity whereby association of said sensor with the structure allows stress to be transferred from said structure to said one or more materials;
at least one device for emitting ultrasound;
a receiver for receiving ultrasound;
wherein said device for emitting ultrasound and said receiver are arranged such that said ultrasound propagates only through said one or more materials when traveling between said device for emitting ultrasound. and said receiver; and
a data processing unit.

18. A sensor system of claim 17, wherein said sensor material has a c/a ratio of at least 1.5.

19. A sensor system as claimed in claim 17, wherein said sensor material is selected from one or materials having MAX phases and mixtures thereof.

20. A sensor system as claimed in claim 18, wherein said sensor material is selected from the group consisting of $Ti_3SiC_2$, $Ti_2AlC$, graphite, hexagonal-boron nitride, mica, and hexagonal metals.

21. A sensor system as claimed in claim 20, wherein the hexagonal metal is selected from the group consisting of Co, Mg, and Ti.

22. A sensor system of claim 17, wherein said data processing unit determines information about a structure from at least one of attenuation and time of flight of said received ultrasound.

23. A sensor system of claim 22, wherein said system comprises calibration data and said data processing unit compares measured data to said calibration data to determine information about a structure.

24. A sensor system of claim 23, wherein said data processing unit determines one or more of a deformation history of said structure, an image of structural deformation of said structure or a maximum deformation experienced by said structure.

* * * * *

UNITED STATES PATENT AND TRADEMARK OFFICE
CERTIFICATE OF CORRECTION

PATENT NO. : 7,917,311 B2  Page 1 of 1
APPLICATION NO. : 12/130234
DATED : March 29, 2011
INVENTOR(S) : Peter Finkel et al.

It is certified that error appears in the above-identified patent and that said Letters Patent is hereby corrected as shown below:

Replace the first paragraph of the patent beginning at column 1, line 7 and ending on column 1, line 10 of the patent with the following paragraph.

This invention was reduced to practice with Government support under Grant Nos. DAAD19-03-1-0213 and W911NF-07-1-0628 awarded by the Army Research Office; the Government is therefore entitled to certain rights to this invention.

Signed and Sealed this
Second Day of August, 2011

David J. Kappos
*Director of the United States Patent and Trademark Office*